(12) United States Patent
Grandel et al.

(10) Patent No.: US 7,087,637 B2
(45) Date of Patent: Aug. 8, 2006

(54) SUBSTITUTED INDOLES WHICH ARE PARP INHIBITORS

(75) Inventors: Roland Grandel, Dossenheim (DE); Wilfried Lubisch, Heidelberg (DE); Michael Kock, Schifferstadt (DE); Thomas Hoger, Edingen-Neckarhausen (DE); Reinhold Muller, Schifferstadt (DE); Sabine Schult, Speyer (DE); Uta Holzenkamp, Lambsheim (DE)

(73) Assignee: BASF AG, Ludwigshafen (DE)

( * ) Notice: Subject to any disclaimer, the term of this patent is extended or adjusted under 35 U.S.C. 154(b) by 366 days.

(21) Appl. No.: 10/275,574

(22) PCT Filed: May 9, 2001

(86) PCT No.: PCT/EP01/05278

§ 371 (c)(1),
(2), (4) Date: Oct. 6, 2003

(87) PCT Pub. No.: WO01/85687

PCT Pub. Date: Nov. 15, 2001

(65) Prior Publication Data

US 2004/0067949 A1    Apr. 8, 2004

(30) Foreign Application Priority Data

May 11, 2000  (DE) ................. 100 22 925

(51) Int. Cl.
A61K 31/40    (2006.01)
C07D 204/42   (2006.01)
C07D 209/12   (2006.01)

(52) U.S. Cl. .............. 514/414; 514/419; 548/492; 548/495

(58) Field of Classification Search ............. 514/414, 514/419; 548/492, 495
See application file for complete search history.

(56) References Cited

U.S. PATENT DOCUMENTS

| | | | |
|---|---|---|---|
| 6,890,947 B1 * | 5/2005 | Binggeli et al. | 514/414 |
| 6,903,117 B1 * | 6/2005 | Farina et al. | 514/323 |
| 6,911,465 B1 * | 6/2005 | Faull et al. | 514/419 |
| 6,916,841 B1 * | 7/2005 | Seehra et al. | 514/419 |
| 6,919,344 B1 * | 7/2005 | Lebaut et al. | 514/256 |
| 6,933,316 B1 * | 8/2005 | Hsieh et al. | 514/419 |
| 6,939,890 B1 * | 9/2005 | Harper et al. | 514/419 |
| 6,951,832 B1 * | 10/2005 | Kuroki et al. | 503/227 |
| 6,951,849 B1 * | 10/2005 | Kelly et al. | 514/210.21 |
| 6,958,348 B1 * | 10/2005 | Koya et al. | 514/299 |
| 6,984,657 B1 * | 1/2006 | Faull et al. | 514/419 |
| 6,987,122 B1 * | 1/2006 | Menta et al. | 514/419 |

FOREIGN PATENT DOCUMENTS

| | | |
|---|---|---|
| EP | 1 127 874 | 2/2001 |
| WO | WO 97/04771 | 2/1997 |
| WO | WO 98/06703 | 2/1998 |
| WO | WO 00/29384 | 5/2000 |
| WO | WO 01/85687 | 11/2001 |

OTHER PUBLICATIONS

K. Ikai et al., *J. Histochem. Cytochem.*. 1983, 31, 1261-1264.
M.S. Satoh et al., *Nature*, 1992, 356, 356-358.
S. Shall, *Adv. Radiat. Biol.* 1984, 11, 1-69.
C. Thiemermann et al., *Proc. Natl. Acad, Sci. USA* 1997, 94, 679-683.
G. Chen et al. *Cancer Chemo. Pharmacol.* 1988, 22, 303.
D. Weltin et al., *Int. J. Immunopharmacol*, 1995, 17, 265-271.
H. Kroger et al., *Inflammation* 1996, 20, 203-215.
W. Ehrlich et al., *Rheumatol Int.* 1995, 15, 171-172.
C. Szabo et al., *Proc. Natl. Acad. Sci. USA* 1998, 95, 3867-3872.
S. Cuzzocrea et al., *Eur. J. Pharmacol.* 1998, 342, 67-76.
S. Cuzzocrea et al., *Br. J. Pharmacol* 1997, 121 1065-1074.
V. Burkart et al., *Nature Med.* 1999, 5, 314-319.
Kasahara et al., *J. Chem, Tech. Biotechnol.* 1986, 36, 562-654.
Kasahara et al. *J. Heterocyclic Chem.* 1987, 24, 1555-1556.
Oikawa et al. *J. Org. Chem.* 1976, 41, 1118-1124.
Black et al., *Tetrahedron*, 1994, 50, 10497-10508.
Brown et al., *J. Chem. Soc.* 1958, 1843.
International Search Report dated Sep. 27, 2001.
International Search Report dated Oct. 12, 2001.

* cited by examiner

*Primary Examiner*—Deborah C. Lambkin
(74) *Attorney, Agent, or Firm*—Wood, Phillips, Katz, Clark & Mortimer

(57) ABSTRACT

The present invention relates to novel indole derivatives, to their preparation and to their use, as inhibitors of the enzyme poly(ADP-ribose)polymerase or PARP (EC 2.4.2.30), for producing drugs.

21 Claims, No Drawings

SUBSTITUTED INDOLES WHICH ARE PARP INHIBITORS

The present invention relates to novel indole derivatives, to their preparation and to their use, as inhibitors of the enzyme poly(ADP-ribose)polymerase or PARP (EC 2.4.2.30), for producing drugs.

Poly(ADP-ribose)polymerase (PARP), or, as it is also termed, poly(ADP-ribose)synthase (PARS), is a regulatory enzyme which is found in cell nuclei (K. Ikai et al., *J. Histochem. Cytochem.* 1983, 31, 1261–1264). It is assumed that PARP plays a role in the repair of DNA breaks (M. S. Satoh et al., *Nature* 1992, 356, 356–358). Damage to, or breaks in, DNA strands activate the enzyme PARP which, when it is activated, catalyzes the transfer of ADP-ribose from NAD (S. Shaw, *Adv. Radiat. Biol.*, 1984, 11, 1–69). In connection with this, nicotinamide is released from the NAD. The nicotinamide is converted once again, by other enzymes, into NAD with consumption of the energy carrier ATP. Accordingly, hyperactivation of PARP would result in an unphysiologically high consumption of ATP, with this leading, in the extreme case, to cell damage and cell death.

It is known that free radicals such as superoxide anion, NO and hydrogen peroxide, can give rise to DNA damage in cells and thereby activate PARP. Large quantities of free radicals are observed to be formed in a number of pathophysiological states, and it is assumed that this accumulation of free radicals leads or contributes to the observed cell or organ damage. While these pathophysiological states include, for example, ischemic states of organs as seen in association with stroke, cardiac infarction (C. Thiemermann et al., *Proc. Natl. Acad. Sci. USA,* 1997, 94, 679–683) or ischemia of the kidneys, they also include reperfusion damage as occurs, for example, after lysis of a cardiac infarction (see above: C. Thiemermann et al.). Consequently, inhibition of the enzyme PARP could be a means of at least partially preventing or alleviating this damage. Consequently, PARP inhibitors could represent a novel therapeutic principle for treating a number of diseases.

The enzyme PARP exerts an influence on the repair of DNA damage and could consequently also play a role in the therapy of cancer diseases since a higher potential effect on tumor tissue was observed in combination with cytostatically active substances (G. Chen et al. *Cancer Chemo. Pharmacol.* 1988, 22, 303).

Furthermore, it has been found that PARP inhibitors are able to exhibit an immunosuppressive effect (D. Weltin et al. *Int. J. Immunopharmacol.* 1995, 17, 265–271).

It has also been discovered that PARP is involved in immunological diseases or disorders in which the immune system plays an important role, such as rheumatoid arthritis and septic shock, and that PARP inhibitors are able to exhibit a favorable effect on the course of the disease (H. Kröger et al. *Inflammation* 1996, 20, 203–215; W. Ehrlich et al. *Rheumatol. Int.* 1995, 15, 171–172; C. Szabo et al., *Proc. Natl. Acad. Sci. USA* 1998, 95, 3867–3872; S. Cuzzocrea et al. *Eur. J. Pharmacol.* 1998, 342, 67–76).

Furthermore, the PARP inhibitor 3-aminobenzamide exhibited protective effects in a model of circulatory shock (S. Cuzzocrea et al., *Br. J. Pharmacol.* 1997, 121, 1065–1074).

There are also experimental indications that inhibitors of the enzyme PARP could be useful agents for treating diabetes mellitus (V. Burkart et al. *Nature Med.* 1999, 5, 314–319).

2-Phenylindoles have been described frequently in the organic synthesis literature. On the other hand, only a few examples are known which carry carboxylic acid derivatives in the 4 or 7 position. Thus, 2-phenylindoles containing a carboxylic acid or carboxylic ester function in the 4, 5 and 6 positions were described in Kasahara et al. J. Chem. Tech. Biotechnol. 1986, 36, 562–564 and Kasahara et al. J. Heterocyclic Chem. 1987, 24, 1555–1556. 2-Phenylindoles containing a 4- or 7-carboxamide function, which, however, carries additional alkyl or aryl substituents, were prepared in Oikawa et al. J. Org. Chem 1976, 41, 1118–1124. 7-Amido-2-phenylindoles which were additionally substituted on the indole were described in Black et al. Tetrahedron, 1994, 50, 10497–10508.

The compounds according to the invention of the general formulae I–II, which are dealt with in this present publication, have not been described previously and are consequently novel.

The present invention provides a compound of the formula I or II

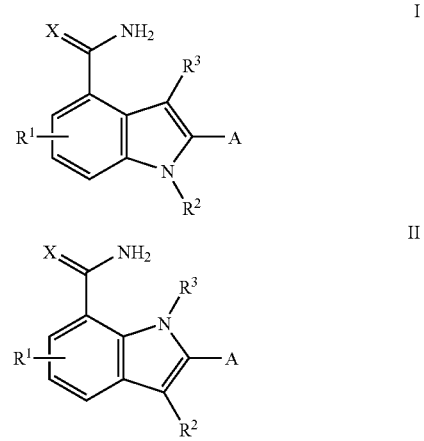

where
X can be S, O and NH, and
$R^1$ is hydrogen, chlorine, fluorine, bromine, iodine, branched or unbranched $C_1$–$C_6$-alkyl, OH, $CF_3$, CN, $NR^{11}R^{12}$ or NH—CO—$R^{13}$, with $R^{11}$ and $R^{12}$, independently of each other, being hydrogen or $C_1$–$C_4$-alkyl, and $R^{13}$ being hydrogen, $C_1$–$C_4$-alkyl, $C_1$–$C_4$-alkylphenyl or phenyl, and
$R^2$ is hydrogen, branched or unbranched $C_1$–$C_6$-alkyl, $C_1$–$C_4$-alkylphenyl or phenyl, and
$R^3$ is hydrogen, branched or unbranched $C_1$–$C_6$-alkyl, $C_1$–$C_4$-alkylphenyl, phenyl, COOH, COO—$C_1$–$C_4$-alkyl or $CONH_2$, with it being possible for each carbon atom in the alkyl chains to additionally carry one or two of the following substituents:
OH, O—$C_1$–$C_4$-alkyl, $NR^{11}R^{12}$, COOH or COO—$C_1$–$C_4$-alkyl, and
A can be an unsaturated, saturated or partially unsaturated monocyclic, bicyclic or tricyclic ring having at most 15 carbon atoms,
or an unsaturated, saturated or partially unsaturated monocyclic, bicyclic or tricyclic ring having at most 14 carbon atoms and from 0 to 5 nitrogen atoms, from 0 to 2 oxygen atoms and/or from 0 to 2 sulfur atoms, which can in each case be additionally substituted by a $R^4$ radical and at most 3 $R^5$ radicals, and
one or two carbon atoms and/or sulfur atoms may furthermore carry one or two =O groups, and $R^4$ is hydrogen or -(D)p-(E)s-($F^1$)q-$G^1$-($F^2$)r-$G^2$-$G^3$, wherein when A is phenyl and p and s is 0, $G^2$ is a bond and $R^5$ is not $NR^{11}R^{12}$, and D is S, $NR^{43}$ or O, E is phenyl,

—$SO_2$—, —$SO_2NH$—, —NHCO—, —CONH—, —$NHSO_2$—, —$NHCOCH_2X_4$, and $X^4$ can be S, O or NH, and $F^1$ can be a straight-chain or branched, saturated or unsaturated $C_1$–$C_8$-group, and $F^2$ independent of $F^1$ may have the same meaning as $F^1$, and $G^1$ can be a bond or a saturated, partially unsaturated or unsaturated monocaclic, bicyclic or tricyclic ring with at most 15 carbon atoms, a saturated, partially unsaturated or unsaturated monocyclic, bicyclic or tricyclic ring with at most 14 carbon atoms and 0 to 5 nitrogen atoms, 0 to 2 oxygen atoms and/or 0 to 2 sulfur atoms, which each may be substituted with at most three different or equal $R^5$ radicals and wherein one or two carbon and/or sulfur atoms may furthermore carry one or two =O groups, and $G^2$ can be $NR^{41}R^{42}$ and

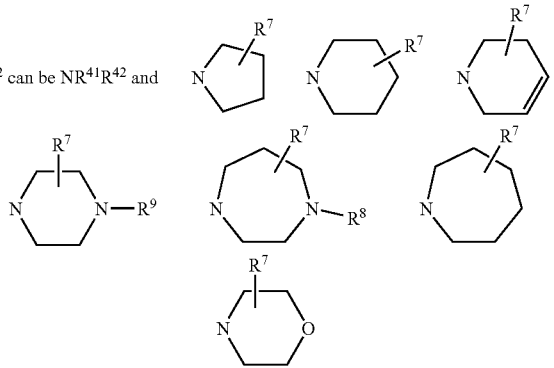

or a bond, and $G^3$ can be hydrogen, a saturated, partially unsaturated or unsaturated monocyclic, bicyclic or tricyclic rig with at most 15 carbon atoms, a saturated, partially unsaturated or unsaturated monocyclic, bicyclic or tricyclic ring with at most 14 carbon atoms and 0 to 5 nitrogen atoms, 0 to 2 oxygen atoms and/or 0 to 2 sulfur atoms, which each may be substituted with at most three different or equal $R^5$ radicals and wherein one or two carbon and/or sulfur atoms may furthermore carry one or two =O groups, and p can be 0 or 1, and s can be 0 or 1, and q can be 0 or 1, and r can be 0 or 1, and $R^{41}$ can be hydrogen, $C_1$–$C_6$-alkyl, wherein every carbon atom may carry up to two $R^6$ radicals, phenyl, which may additionally carry at most two $R^6$ radicals, or $(CH_2)_t$-K, and $R^{42}$ can be hydrogen, $C_1$–$C_6$-alkyl, —CO—$R^8$, $SO_2$—$R^8$, $SO_2NH_2$, —(C=N)—$R^8$ or —(C=N)—$NHR^8$, —$CO_2$—$R^8$, and $R^{43}$ can be hydrogen or $C_1$–$C_4$-alkyl, and t can be 1,2,3 or 4, and K can be $NR^{11}R^{12}$, $NR^{11}$—$C_1$–$C_4$-alkyl-phenyl, pyrrolidine, piperidine, 1,2,5,6-tetrahydropyridine, morpholine, homopiperidine, piperazine, which may be substituted with one $C_1$–$C_6$-alkyl group, or homopiperazine, which may be substituted with one $C_1$–$C_6$-alkyl group, and $R^5$ can be hydrogen, chlorine, fluorine, bromine, iodine, branched or unbranched $C_1$–$C_6$-alkyl, OH, nitro, $CF_3$, CN, $NR^{11}R^{12}$, NH—CO—$R^{13}$, O—$C_1$–$C_4$-alkyl, $COR^8$, $C_1$–$C_4$-alkyl-phenyl, phenyl, $CO_2$—$C_1$–$C_4$-alkyl, S—$C_1$–$C_4$-alkyl, wherein every carbon atom of the alkyl chains may additionally carry up to two $R^6$ radicals and wherein the alkyl chains may furthermore be unsaturated, and $R^6$ can be hydrogen, chlorine, fluorine, bromine, iodine, branched or unbranched $C_1$–$C_6$-alkyl, OH, nitro, $CF_3$, CN, $NR^{11}R^{12}$, NH—CO—$R^{13}$ or O—$C_1$–$C_4$-alkyl, and $R^7$ can be hydrogen, $C_1$–$C_6$-alkyl, phenyl, where the ring can be additionally substituted by up to two $R^{71}$ radicals, or an amine $NR^{11}R^{12}$ or a cyclic, saturated amine having 3 to 7 members, such as pyrrolidine, piperidine, etc., which may be substituted with one $C_1$–$C_6$ alkyl group, and homopiperazine, which may be substituted with one $C_1$–$C_6$-alkyl group, wherein groups $R^{11}$, $R^{12}$ and $R^{13}$ in K, $R^5$, $R^6$ and $R^7$ may have independently the same meaning as $R^1$ $R^{71}$ can be OH, $C_1$–$C_6$-alkyl, O—$C_1$–$C_4$-alkyl, chlorine, bromine, iodine, fluorine, $CF_3$, nitro or $NH_2$, and $R^8$ can be $C_1$–$C_6$-alkyl, $CF_3$, phenyl or $C_1$–$C_4$-alkylphenyl, where the ring can be additionally substituted by up to two $R^{81}$ radicals, and $R^{81}$ can be OH, $C_1$–$C_6$-alkyl, O—$C_1$–$C_4$-alkyl, chlorine, bromine, iodine, fluorine, $CF_3$, nitro or $NH_2$, and $R^9$ can be hydrogen, $C_1$–$C_6$-alkyl, $CO_2$—$C_1$–$C_4$-alkyl, $COR^8$, $CO_2$—$C_1$–$C_4$-alkyl-phenyl, $SO_2$-phenyl, $C_1$–$C_4$-alkylphenyl or phenyl, where the phenyl rings can be additionally substituted by up to two $R^{91}$ radicals, and $R^{91}$ can be OH, $C_1$–$C_6$-alkyl, O—$C_1$–$C_4$-alkyl, chlorine, bromine, iodine, fluorine, $CF_3$, nitro or $NH_2$, with the compounds 4-carboxamido-2-(1-ethylpiperidin-4-yl)-1H-indole and 4-carboxamido-2-(1-ethyl-1,2,3,6-tetrahydropyridin-4-yl)-1H-indole being excluded, and also their tautomeric forms, possible enantiomeric and diastereomeric forms, and their prodrugs.

Preferred is a compound of the formula I or II wherein

X is O, and $R^1$ is hydrogen, and all the other variables have the abovementioned meanings.

Preferred is a compound of the formula I or II wherein

X is O, and $R^1$ is hydrogen, and

A is phenyl, cyclohexyl, piperidine, pyridine, pyrimidine or pyrazine, which compounds can be additionally substituted by one $R^4$ or at most 2 $R^5$, and all the other variables have the meanings as given in claim 1.

In particular preferred is a compound of the formula I or II wherein

X is O, and $R^1$ is hydrogen, and

A is phenyl, cyclohexyl, piperidine, pyridine, pyrimidine or pyrazine, which compounds can be additionally substituted by one $R^4$ or at most 2 $R^5$, and $R^4$ is -Dp-$F_{0,1}$-$G^2$-$G^3$ with $G^3$ equal hydrogen, wherein, when A is phenyl and p is 1, D is not $NR^{43}$ and $R^5$ is not $NR^{11}R^{12}$, and when A is phenyl and p is 0, $G^2$ is a bond and $R^5$ is not $NR^{11}R^{12}$, D is O or $NR^{43}$, where $R^{43}$ is hydrogen or $C_1$–$C_3$-alkyl, and F is $C_2$–$C_4$-alkyl, and $G^2$ has the same meaning as given above, and $R^5$ has the same meaning as given above.

The use of compounds of the general formulae I and II for producing drugs for treating neurodegenerative diseases and neuronal damage is also claimed, with $R^1$, $R^2$, $R^3$ and X having the same meanings as given above and A is hydrogen.

The compounds of the formulae I, II can be employed as racemates, as enantiomerically pure compounds or as diastereomers. If enantiomerically pure compounds are desired, they can be obtained, for example, by carrying out a classical racemate resolution using a suitable optically active base or acid and the compounds of the formula I or their intermediates.

The present invention also relates to mesomeric or tautomeric compounds of the formulae I, II.

The present invention furthermore relates to physiologically tolerated salts of the compounds I, II which can be obtained by reacting compounds I, II with a suitable acid or base. Examples of suitable acids and bases are listed in Fortschritte der Arzneimittelforschung (Advances in Drug Research), 1966, Birkhäuser Verlag, Vol. 10, pp. 224–285. They include, for example, hydrochloric acid, citric acid, tartaric acid, lactic acid, phosphoric acid, methanesulfonic acid, acetic acid, formic acid, maleic acid, fumaric acid, etc., and sodium hydroxide, lithium hydroxide, potassium hydroxide and Tris.

Prodrugs are understood as being compounds which are metabolized in vivo into compounds of the general formulae I, II. Typical prodrugs are phosphates, carbamates of aminoacids, esters and other compounds.

The indole derivatives I, II according to the invention can be prepared in a variety of ways. Possible methods of synthesis follow those described in the above-listed literature references. Scheme 1 is intended to illustrate the synthesis strategy which is pursued in this connection.

Ester 1 is reacted with a styrene derivative in a palladium-catalyzed reaction. Where Y=NR$_2$, the ring closure to form indole 3 takes place under aqueous/acid conditions. Where Y=H, the ring closure takes place after N-tosylation by palladium catalysis. The indole 3 is obtained by basic elimination of the N-tosyl group. The ester is reacted, at elevated temperatures, preferably from 80 to 130° C., with hydrazine in polar solvents such as the alcohols butanol and ethanol or else dimethylformamide. The hydrazide which accumulates in this connection is then reduced to the amide 4 under reductive conditions, such as using Raney nickel in alcohols under reflux.

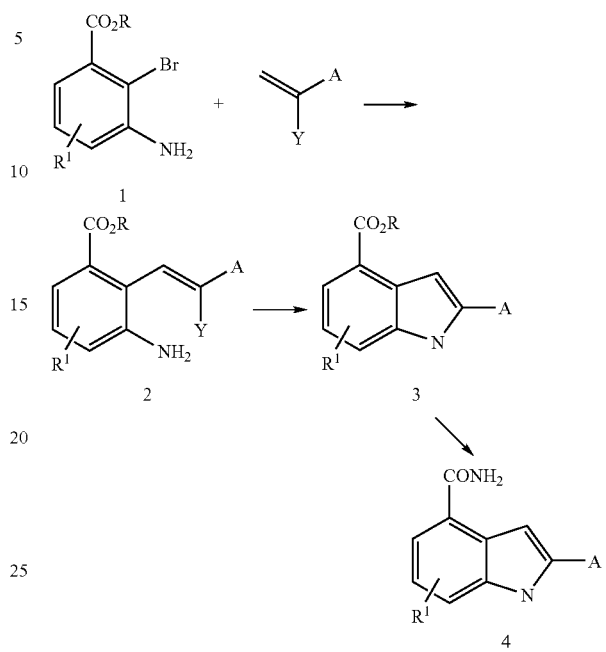

Scheme 1

The substituted indole derivatives I, II which are contained in the present invention are inhibitors of the enzyme poly(ADP-ribose)polymerase or PARP (EC 2.4.2.30).

The inhibitory effect of the substituted indole derivatives I, II was ascertained using an enzyme test which was already known in the literature, with a $K_i$ value being determined as the measure of activity. In this way, the indole derivatives I, II were quantitatively tested for their inhibitory effect on the enzyme poly(ADP-ribose)polymerase or PARP (EC 2.4.2.30).

The substituted indole derivatives of the general formulae I, II are inhibitors of poly(ADP-ribose)polymerase (PARP) or, as it is also termed, poly(ADP-ribose)synthase (PARS) and can consequently be used for the treatment and prophylaxis of diseases which are linked to an increased activity of these enzymes.

The compounds of the formulae I, II can be employed for producing drugs for treating damage which occurs following ischemias and for prophylaxis where ischemias of various organs are expected.

Accordingly, the present indole derivatives of the general formulae I, II can be used for the treatment and prophylaxis of neurodegenerative diseases which occur following ischemia, trauma (craniocerebral trauma), hemorrhages, subarachnoidal bleeding and stroke, and of neurodegenerative diseases such as multiple infarct dementia, Alzheiner's disease and Huntington's disease, and of epilepsies, in particular of generalized epileptic attacks such as petit mal and tonic/clonic attacks and partial epileptic attacks, such as temporal lobe, and complex partial attacks, and, furthermore, for the treatment and prophylaxis of damage to the heart following cardiac ischemias and damage to the kidneys following renal ischemias, for example of acute kidney insufficiency, of acute kidney failure and of damage which occurs during and after a kidney transplant. Furthermore, the compounds of the general formulae I, II can be used for treating acute myocardial infarction and damage which occurs during and after its lysis by medical treatment (for example using TPA, Reteplase or Streptokinase or mechanically using a laser or rotablator), and of microinfarctions during and after heart valve replacement, aneurysm resections and heart transplants The present indole derivatives I, II can likewise be used for treating revascularization of critically stenosed coronary arteries, for example in PCTA and bypass operations, and critically stenosed peripheral arteries, for example arteries of the leg. Furthermore, the indole derivatives I, II can be of use in the chemotherapy of tumors and their metastasization and be used for treating inflammations and rheumatic diseases, for example rheumatoid arthritis, and also for treating diabetes mellitus.

The drug preparations according to the invention contain a therapeutically effective quantity of the compounds I, II in addition to the customary pharmaceutical adjuvants.

For local external use, for example in powders, ointments or sprays, the active compounds can be present at the customary concentrations. As a rule, the active compounds are present in a quantity of from 0.001 to 1% by weight, preferably of from 0.001 to 0.1% by weight.

For internal use, the preparations are administered in individual doses. In an individual dose, from 0.1 to 100 mg is/are administered per kg of body weight. The preparations may be administered daily in one or more doses, depending on the nature and severity of the diseases.

In addition to the active compound, the drug preparations according to the invention comprise the customary excipients and diluents which correspond to the desired mode of administration. For local external use, it is possible to employ adjuvants which are customary in pharmaceutical technology, such as ethanol, isopropanol, ethoxylated castor oil, ethoxylated hydrated castor oil, polyacrylic acid, polyethylene glycol, polyethylene glycostearate, ethoxylated fatty alcohols, paraffin oil, vaseline and lanolin. Lactose, propylene glycol, ethanol, starch, talc and polyvinylpyrrolidone are, for example, suitable for internal use.

Furthermore the preparations can comprise antioxidants such as tocopherol and butylated hydroxyanisole and also butylated hydroxytoluene, taste-improving additives, stabilizers, emulsifiers and glidants.

The substances which the preparation contains in addition to the active compound, and also the substances employed in producing the pharmaceutical preparations, are toxicologically harmless and compatible with the relevant active compound. The drug preparations are produced in a customary manner, for example by mixing the active compound with other customary excipients and diluents.

The drug preparations may be administered in a variety of modes of administration, for example perorally, parenterally, such as intravenously by infusion, subcutaneously, intraperitoneally and topically. Thus, possible preparation forms are tablets, emulsions, infusion solutions, injection solutions, pastes, ointments, gels, creams, lotions, powders and sprays.

EXAMPLE A

Inhibition of the Enzyme Poly(ADP-ribose)polymerase or PARP (EC 2.4.2.30)

A 96-well microtiter plate (Falcon) is coated with histones (type II-AS; SIGMA H7755). For this, histones are dissolved up to a concentration of 50 µg/ml in carbonate buffer (0.05 M $NaHCO_3$; pH 9.4). The individual wells of the microtiter plate are incubated overnight with in each case 100 µl of this histone solution. The histone solution is then removed and the individual wells are incubated, at room temperature, with 200 µl of a 1% BSA (bovine serum albumin) solution in carbonate buffer for 2 hours. The plate is then washed three times with washing buffer (0.05% Tween10 in PBS). For the enzyme reaction, 50 µl of the enzyme reaction solution (5 µl of reaction buffer (1M Tris-HCl, pH 8.0, 100 mM $MgCl_2$, 10 mM DTT), 0.5 µl of PARP (c=0.22 µg/µl), 4 µl of activated DNA (SIGMA D-4522, 1 mg/ml in water), 40.5 µl of $H_2O$) are preincubated, in each well, for 10 minutes with 10 µl of an inhibitor solution. The enzyme reaction is started by adding 40 µl of a substrate solution (4 µl of reaction buffer (see above), 8 µl of NAD solution (100 µM in $H_2O$), 28 µl of $H_2O$). The reaction time is 20 minutes at room temperature. The reaction is stopped by washing three times with washing buffer (see above). There then follows a one-hour incubation at room temperature, during which time the plate is incubated with a specific anti-poly-ADP-ribose antibody. The antibody employed was a monoclonal "10OH" anti-poly (ADP-ribose) antibody (Kawamaitsu H et al. (1984) Monoclonal antibodies to poly (adenosine diphosphate ribose) recognize different structures. Biochemistry 23, 3771–3777) Polyclonal antibodies can be used in exactly the same way.

The antibodies were used in a 1:5000 dilution in antibody buffer (1% BSA in PBS; 0.05% Tween20). After the plate has been washed three times with washing buffer, there then follows a one-hour incubation at room temperature with the secondary antibody. In this case, use was made, for the monoclonal antibody, of an antimouse IgG coupled to peroxidase (Boehringer Mannheim) and, for the rabbit antibody, of an anti-rabbit IgG coupled to peroxidase (SIGMA A-6154), with each of these secondary antibodies being used in a 1:10000 dilution in antibody buffer. After the plate has been washed three times with washing buffer, the color reaction is effected using 100 µl of color reagent (SIGMA, TMB Readymix, T8540)/well at room temperature for approx. 15 min. The color reaction is stopped by adding 100 µl of 2M $H_2SO_4$. A measurement is then taken immediately (450 nm against 620 nm; "Easy Reader" ELISA plate reading appliance EAR340AT, SLT Labinstruments, Austria). The $IC_{50}$ value of an inhibitor under measurement is the concentration of the inhibitor at which the change in color concentration is half the maximum.

The following compounds according to the invention can be prepared using the above-described methods:

2-(4(4-n-Propyl-piperazin-1-yl)-phenyl)-1H-indol-4-carboxamid 2-(4-Piperazin-1-yl-phenyl)-1H-indol-4-carboxamid 2-(4(4-Isopropyl-piperazin-1-yl)-phenyl)-1H-indol-4-carboxamid 2-(4(4-Benzyl-piperazin-1-yl)-phenyl)-1H-indol-4-carboxamid 2-(4(4-n-Butyl-piperazin-1-yl)-phenyl)-1H-indol-4-carboxamid 2-(4(4-Ethyl-piperazin-1-yl)-phenyl)-1H-indol-4-carboxamid 2-(4-(2-N,N-Dimethylamino-eth-1-yloxy)-phenyl)-1H-indol-4-carboxamid 2-(4-(2-Pyrrolidinl-yl-eth-1-yloxy)-phenyl)-1H-indol-4-carboxamid 2-(4-(2-Piperidin-yl-eth-1-yloxy)-phenyl)-1H-indol-4-carboxamid 2-(4-(2-Piperazin-yl-eth-1-yloxy)-phenyl)-1H-indol-4-carboxamid 2-(4-(2-(4-Methyl-piperazin-1-yl)-eth-1-yloxy)-phenyl)-1H-indol-4-carboxamid 2-(4-(2-(4-Propyl-piperazin-1-yl)-eth-1-yloxy)-phenyl)-1H-indol-4-carboxamid
2-(4-(2-(4-Ethyl-piperazin-1-yl)-eth-1-yloxy)-phenyl)-1H-indol-4-carboxamid
2-(4-(2-(4-Benzyl-piperazin-1-yl)-eth-1-yloxy)-phenyl)-1H-indol-4-carboxamid
2-(4-(2-(4-Acetamido-piperazin-1-yl)eth-1-yloxy)-phenyl)-1H-indol-4-carboxamid
2-(4-(2-(4-Benzamido-piperazin-1-yl)-eth-1-yloxy)-phenyl)-1H-indol-4-carboxamid
2-(4-Homopiperazin-1-yl-phenyl)-1H-indol-1-carboxamid
2-(4(4-Methylhomopiperazin-1-yl)-phenyl)-1H-indol-4-carboxamid
2-(4(4-Benzylhomopiperazin-1-yl)-phenyl)-1H-indol-4-carboxamid
2-(4-(4-n-Butyl-homopiperazin-1-yl)-phenyl)-1H-indol-4-carboxamid
2-(4(4-Ethylhomo-piperazin-1-yl)-phenyl)-1H-indol-4-carboxamid
2-(4-Methoxy-phenyl)-1H-indol-4-carboxamid
2-(4-Chlor-phenyl)-1H-indol-4-carboxamid
2-(4-Amino-phenyl)-1H-indol-4-carboxamid
2-(4-Methyl-phenyl)-1H-indol-4-carboxamid
2-(4-Phenyl-phenyl)-1H-indol-4-carboxamid
2-(4-Isopropyl-phenyl)-1H-indol-4-carboxamid
2-(4-Flour-phenyl)-1H-indol-4-carboxamid
2-(4-Triflourmethyl-phenyl)-1H-indol-4-carboxamid
2-(3-Methoxy-phenyl)-1H-indol-4-carboxamid
2-(3-Chlor-phenyl)-1H-indol-4-carboxamid
2-(3-Amino-phenyl)-1H-indol-4-carboxamid
2-(3-Methyl-phenyl)-1H-indol-4-carboxamid
2-(3-Phenyl-phenyl)-1H-indol-4-carboxamid
2-(3-Isopropyl-phenyl)-1H-indol-4-carboxamid
2-(3-Flour-phenyl)-1H-indol-4-carboxamid
2-(3-Triflourmethyl-phenyl)-1H-indol-4-carboxamid
2-Piperidin-4-yl-1H-indol-4-carboxamid
2-(1-Methyl-piperidin-4-yl)-1H-indol-4-carboxamid
2-(1-n-Propyl-piperidin-4-yl)-1H-indol-4-carboxamid
2-(1-Benzyl-piperidin-4-yl)-1H-indol-4-carboxamid
2-(1-n-Butyl-piperidin-4-yl)-1H-indol-4-carboxamid
2-(1-Isopropyl-piperidin-4-yl)-1H-indol-4-carboxamid
2-Pyridin-4-yl-1H-indol-4-carboxamid
2-Pyridin-3-yl-1H-indol-4-carboxamid
2-Pyridin-2-yl-1H-indol-4-carboxamid
2-Thien-2-yl-1H-indol-4-carboxamid
2-Thien-3-yl-1H-indol-4-carboxamid
2-Indol-3-yl-1H-indol-4-carboxamid
2-Indol-5-yl-1H-indol-4-carboxamid
2-Indol-2-yl-1H-indol-4-carboxamid
2-Chinolin-3-yl-1H-indol-4-carboxamid
2-Chinolin-2-yl-1H-indol-4-carboxamid
2-Chinolin-4-yl-1H-indol-4-carboxamid
2-Isochinolin-1-yl-1H-indol-4-carboxamid
2-Isochinolin-3-yl-1H-indol-4-carboxamid
2-Chinoxalin-2-yl-1H-indol-1-carboxamid
2-Naphth-2-yl-1H-indol-4-carboxamid
2-Naphth-1-yl-1H-indol-4-carboxamid
2-(2(N,N-Dimethylamino)-eth-1-ylamino)-phenyl)-1H-indol-4-carboxamid
2-(2(N,N-Diethylamino)-eth-1-ylamino)-phenyl)-1H-indol-4-carboxamid
2-(2-Piperidin-1-yl-eth-1-ylamino)-phenyl)-1H-indol-4-carboxamid
2-(2-Pyrrolidin-1-yl-eth-1-ylamino)-phenyl)-1H-indol-4-carboxamid
2-(3(N,N-Dimethylamino)-prop-1-ylamino)-phenyl)-1H-indol-4-carboxamid
2-(3(N,N-Diethylamino)-prop-1-ylamino)-phenyl)-1H-indol-4-carboxamid
2-(3-Piperidin-1-yl-prop-1-ylamino)-phenyl)-1H-indol-4-carboxamid
2-(3-Pyrrolidin-1-yl-prop-1-ylamino)-phenyl)-1H-indol-4-carboxamid
2-Cyclohexyl-1H-indol-4-carboxamid
2-(cis-4-Amino-cyclohex-1-yl)-1H-indol-4-carboxamid
2-(4-Methoxy-cyclohex-1-yl)-1H-indol-4-carboxamid
2-(4(4-n-Propyl-piperazin-1-yl)-phenyl)-1H-indol-7-carboxamid
2-(4-Piperazin-1-yl-phenyl)-1H-indol-7-carboxamid
2-(4(4-Isopropyl-piperazin-1-yl)-phenyl)-1H-indol-7-carboxamid
2-(4(4-Benzyl-piperazin-1-yl)-phenyl)-1H-indol-7-carboxamid
2-(4(4-n-Butyl-piperazin-1-yl)-phenyl)-1H-indol-7-carboxamid
2-(4(4-Ethyl-piperazin-1-yl)-phenyl)-1H-indol-7-carboxamid
2-(4-(2-N,N-Dimethylamino-eth-1-yloxy)-phenyl)-1H-indol-7-carboxamid
2-(4-(2-Pyrrolidin-1-yl-eth-1-yloxy)-phenyl)-1H-indol-7-carboxamid
2-(4-(2-Piperidin-1-yl-1-yloxy)-phenyl)-1H-indol-7-carboxamid
2-(4-(2-Piperazin-1-yl-eth-1-yloxy)-phenyl)-1H-indol-7-carboxamid
2-(4-(2-(4-Methyl-piperazin-1-yl)-eth-1-yloxy)-phenyl)-1H-indol-7-carboxamid
2-(4-(2-(4-Propyl-piperazin-1-yl)-eth-1-yloxy)-phenyl)-1H-indol-7-carboxamid
2-(4-(2-(4-Ethyl-piperazin-1-yl)-eth-1-yloxy)-phenyl)-1H-indol-7-carboxamid
2-(4-(2-(4-Benzyl-piperazin-1-yl)-eth-1-yloxy)-phenyl)-1H-indol-7-carboxamid
2-(4-(2-(4-Acetamido-piperazin-1-yl)-eth-1-yloxy)-phenyl)-1H-indol-7-carboxamid
2-(4-(2-(4-Benzamido-piperazin-1-yl)-eth-1-yloxy)-phenyl)-1H-indol-7-carboxamid
2-(4-Homopiperazin-1-yl-phenyl)-1H-indol-7-carboxamid
2-(4(4-Methylhomopiperazin-1-yl)-phenyl)-1H-indol-7-carboxamid
2-(4(4-Benzylhomopiperazin-1-yl)-phenyl)-1H-indol-7-carboxamid
2-(4-(4-n-Butyl-homopiperazin-1-yl)-phenyl)-1H-indol-7-carboxamid
2-(4(4-Ethylhomo-piperazin-1-yl)-phenyl)-1H-indol-7-carboxamid
2-(4-Methoxy-phenyl)-1H-indol-7-carboxamid
2-(4-Chlor-phenyl)-1H-indol-7-carboxamid
2-(4-Amino-phenyl)-1H-indol-7-carboxamid
2-(4-Methyl-phenyl)-1H-indol-7-carboxamid
2-(4-Phenyl-phenyl)-1H-indol-7-carboxamid
2-(4-Isopropyl-phenyl)-1H-indol-7-carboxamid
2-(4-Flour-phenyl)-1H-indol-7-carboxamid
2-(4-Triflourmethyl-phenyl)-1H-indol-7-carboxamid
2-(3-Methoxy-phenyl)-1H-indol-7-carboxamid
2-(3-Chlor-phenyl)-1H-indol-7-carboxamid
2-(3-Amino-phenyl)-1H-indol-7-carboxamid
2-(3-Methyl-phenyl)-1H-indol-7-carboxamid
2-(3-Phenyl-phenyl)-1H-indol-7-carboxamid
2-(3-Isopropyl-phenyl)-1H-indol-7-carboxamid
2-(3-Flour-phenyl)-1H-indol-7-carboxamid
2-(3-Triflourmethyl-phenyl)-1H-indol-7-carboxamid
2-Piperidin-4-yl-1H-indol-7-carboxamid
2-(1-Methyl-piperidin-4-yl)-1H-indol-7-carboxamid 2-(1-n-Propyl-piperidin-4-yl)-1H-indol-7-carboxamid
2-(1-Benzyl-piperidin-4-yl)-1H-indol-7-carboxamid
2-(1-n-Butyl-piperidin-4-yl)-1H-indol-7-carboxamid
2-(1-Isopropyl-piperidin-4-yl)-1H-indol-7-carboxamid
2-Pyridin-4-yl-1H-indol-7-carboxamid
2-Pyridin-3-yl-1H-indol-7-carboxamid
2-Pyridin-2-yl-1H-indol-7-carboxamid
2-Thien-2-yl-1H-indol-7-carboxamid
2-Thien-3-yl-1H-indol-7-carboxamid
2-Indol-3-yl-1H-indol-7-carboxamid
2-Indol-5-yl-1H-indol-7-carboxamid
2-Indol-2-yl-1H-indol-7-carboxamid
2-Chinolin-3-yl-1H-indol-7-carboxamid
2-Chinolin-2-yl-1H-indol-7-carboxamid
2-Chinolin-4-yl-1H-indol-7-carboxamid
2-Isochinolin-1-yl-1H-indol-7-carboxamid
2-Isochinolin-3-yl-1H-indol-7-carboxamid
2-Chinoxalin-2-yl-1H-indol-7-carboxamid
2-Naphth-2-yl-1H-indol-7-carboxamid
2-Naphth-1-yl-1H-indol-7-carboxamid
2-(2(N,N-Dimethylamino)-eth-1-ylamino)-phenyl)-1H-indol-7-carboxamid
2-(2(N,N-Diethylamino)-eth-1-ylamino)-phenyl)-1H-indol-7-carboxamid
2-(2-Piperidin-1-yl-eth-1-ylamino)-phenyl)-1H-indol-7-carboxamid
2-(2-Pyrrolidin-1-yl-eth-1-ylamino)-phenyl)-1H-indol-7-carboxamid
2-(3(N,N-Dimethylamino)-prop-1-ylamino)-phenyl)-1H-indol-7-carboxamid
2-(3(N,N-Diethylamino)-prop-1-ylamino)-phenyl)-1H-indol-7-carboxamid
2-(3-Piperidin-1-yl-prop-1-ylamino)-phenyl)-1H-indol-7-carboxamid
2-(3-Pyrrolidin-1-yl-prop-1-yl-amino-phenyl)-1H-indol-7-carboxamid
2-Cyclohexyl-1H-indol-7-carboxamid
2-(cis-4-Amino-cyclohex-1-yl)-1H-indol-7-carboxamid
2-(4-Methoxy-cyclohex-1-yl)-1H-indol-7-carboxamid The present invention also relates to substituted indole derivatives of the general formulae Ia and IIa

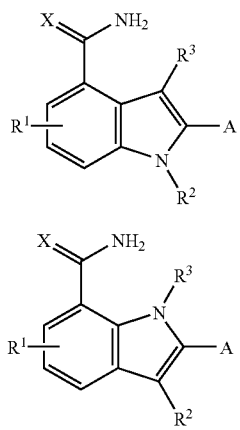

where
X can be S, O and N, and
$R^1$ is hydrogen, chlorine, fluorine, bromine, iodine, branched or unbranched $C_1$–$C_6$-alkyl, OH, $CF_3$, CN, $NR^{11}R^{12}$ or NH—CO—$R^{13}$, with $R^{11}$ and $R^{12}$, independently of each other, being hydrogen or $C_1$–$C_4$-alkyl, and $R^{13}$ being hydrogen, $C_1$–$C_4$-alkyl, $C_1$–$C_4$-alkylphenyl or phenyl, and $R^2$ is hydrogen, branched or unbranched $C_1$–$C_6$-alkyl, $C_1$–$C_4$-alkylphenyl or phenyl, and $R^3$ is hydrogen, branched or unbranched $C_1$–$C_6$-alkyl, $C_1$–$C_4$-alkylphenyl, phenyl, COOH, COO—$C_1$–$C_4$-alkyl or $CONH_2$, with it being possible for each carbon atom in the alkyl chains to additionally carry one or two of the following substituents:
  OH, O—$C_1$–$C_4$-alkyl, $NR^{11}R^{12}$, COOH or COO—$C_1$–$C_4$-alkyl, and A can be an unsaturated or saturated monocyclic, bicyclic or tricyclic ring having at most 15 carbon atoms, such as phenyl, naphthalene, tetrahydronaphthalene, indan, fluorene, carbazole, cyclohexane, or an unsaturated, saturated or partially unsaturated monocyclic, bicyclic or tricyclic ring having at most 14 carbon atoms and from 0 to 5 nitrogen atoms, from 0 to 2 oxygen atoms and/or from 0 to 2 sulfur atoms, such as pyridine, thiophene, quinoline, quinoxaline, furan, imidazole, pyrrole, indole, benzimidazole, pyrimidine, pyrazine, benzofuran, benzothiophene, thiophene, quinazoline or isoxazole, which can in each case be additionally substituted by a $R^4$ radical and at most 3 $R^5$ radicals, and $R^4$ is hydrogen or -(D)$_p$-(E)$_s$-(F)$_q$-G, where
D is S, $NR^{43}$ or O
E is phenyl, and s is 0 or 1, and
G is $NR^{41}R^{42}$ or

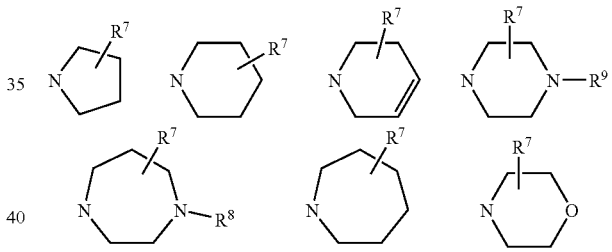

and
p can be 0 or 1, and
F can be a carbon chain of from 1 to 8 C atoms, and
q can be 0 or 1, and
$R^{41}$ can be hydrogen, $C_1$–$C_6$-alkyl, phenyl, which can additionally carry at most two $R^6$ radicals, or $(CH_2)_r$—H, and
$R^{42}$ can be hydrogen, $C_1$–$C_6$-alkyl, —CO—$R^8$, $SO_2$—$R^8$, —(C=N)—$R^8$ or —(C=N)—$NHR^8$, and
$R^{43}$ can be hydrogen or $C_1$–$C_4$-alkyl, and
r can be 1,2,3,4, and
H can be $NR^{11}R^{12}$, $NR^{11}$—$C_1$–$C_4$-alkylphenyl, pyrrolidine, piperidine, 1,2,5,6-tetrahydropyridine, morpholine, homopiperidine, piperazine, which can be additionally substituted by a $C_1$–$C_6$-alkyl radical, or homopiperazine, which can additionally be substituted by a $C_1$–$C_6$-alkyl radical, and $R^5$ can be hydrogen, chlorine, fluorine, bromine, iodine, branched or unbranched $C_1$–$C_6$-alkyl, OH, nitro, $CF_3$, CN, $NR^{11}R^{12}$, NH—CO—$R^{13}$ or O—$C_1$–$C_4$-alkyl, $R^6$ can be hydrogen, chlorine, fluorine, bromine, iodine, branched or unbranched $C_1$–$C_6$-alkyl, OH, nitro, $CF_3$, CN, $NR_{11}R^{12}$, NH—CO—$R^{13}$ or O—$C_1$–$C_4$-alkyl, $R^7$ can be hydrogen, $C_1$–$C_6$-alkyl, phenyl, where the ring can be additionally substituted by up to two $R^{71}$ radicals, or an amine $NR^{11}R^{12}$ or a cyclic, saturated amine having 3 to 7 members, such as pyrrolidine, piperidine, etc., and $R^{71}$ can be OH, $C_1$–$C_6$-alkyl, O—$C_1$–$C_4$-alkyl, chlorine, bromine, iodine, fluorine, $CF_3$, nitro or $NH_2$, and $R^8$ can be $C_1$–$C_6$-alkyl, phenyl or $C_1$–$C_4$-alkylphenyl, where the ring can be additionally substituted by up to two $R^{81}$ radicals, and $R^{81}$ can be OH, $C_1$–$C_6$-alkyl, O—$C_1$–$C_4$-alkyl, chlorine, bromine, iodine, fluorine, $CF_3$, nitro or $NH_2$, and $R^9$ can be hydrogen, $C_1$–$C_6$-alkyl, $C_1$–$C_4$-alkylphenyl or phenyl, where the phenyl rings can be additionally substituted by up to two $R^{91}$ radicals, and $R^{91}$ can be OH, $C_1$–$C_6$-alkyl, O—$C_1$–$C_4$-alkyl, chlorine, bromine, iodine, fluorine, $CF_3$, nitro or $NH_2$, with the compounds 4-carboxamido-2-(1-ethylpiperidin-4-yl)-1H-indole and 4-carboxamido-2-(1-ethyl-1,2,3,6-tetrahydropyridin-4-yl)-1H-indole being excluded, and also their tautomeriic forms, possible enantiomeric and diastereomeric forms, and their prodrugs.

Preference is given to compounds of the formulae Ia and IIa where

X is O, and $R^1$ is hydrogen, and all the other variables have the abovementioned meanings.

Preference is given to compounds of the formulae Ia and IIa where

X is O, and $R^1$ is hydrogen, and

A is phenyl, cyclohexyl, piperidine, pyridine, pyridine or pyrazine, which compounds can be additionally substituted by one $R^4$ or at most 2 $R^5$, and all the other variables have the abovementioned meanings.

Particular preference is given to compounds of the formulae Ia and IIa where

X is O, and $R^1$ is hydrogen, and

A is phenyl, cyclohexyl, piperidine, pyridine, pyrimidine or pyrazine, which compounds can additionally be substituted by one $R^4$ or at most 2 $R^5$, and $R^4$ is -$D_{0.1}$-$F_{0.1}$-G, and D is O or $NR^{43}$, where $R^{43}$ is hydrogen or $C_1$–$C_3$-alkyl, and F is $C_2$–$C_4$-alkyl, and G has the meanings given above, and $R^5$ has the meanings given above.

The use of compounds of the general formulae Ia and IIa for producing drugs for treating neurodegenerative diseases and neuronal damage is also claimed, with $R^1$, $R^2$, $R^3$ and X having the same meanings as above and with it being possible for A to be hydrogen or a $C_1$–$C_6$ alkyl chain.

The compounds of the formulae Ia, IIa can be employed as racemates, as enantiomerically pure compounds or as diastereomers. If enantiomerically pure compounds are desired, they can be obtained, for example, by carrying out a classical racemate resolution using a suitable optically active base or acid and the compounds of the formula I or their intermediates.

The present invention also relates to mesomeric or tautomeric compounds of the formulae Ia, IIa.

The present invention furthermore relates to physiologically tolerated salts of the compounds Ia, IIa which can be obtained by reacting compounds Ia, IIa with a suitable acid or base. Examples of suitable acids and bases are listed in Fortschritte der Arzneimittelforschung (Advances in Drug Research), 1966, Birkhäuser Verlag, Vol. 10, pp. 224–285.

They include, for example, hydrochloric acid, citric acid, tartaric acid, lactic acid, phosphoric acid, methanesulfonic acid, acetic acid, formic acid, maleic acid, fumaric acid, etc., and sodium hydroxide, lithium hydroxide, potassium hydroxide and Tris.

Prodrugs are understood as being compounds which are metabolized in vivo into compounds of the general formulae Ia, IIa. Typical prodrugs are phosphates, carbamates of aminoacids, esters and other compounds.

The indole derivatives Ia, IIa according to the invention can be prepared in a variety of ways. Possible methods of synthesis follow those described in the above-listed literature references. Scheme 2 is intended to illustrate the synthesis strategy which is pursued in this connection.

Ester 1 is reacted with a styrene derivative in a palladium-catalyzed reaction. Where Y=$NR_2$, the ring closure to form indole 3 takes place under aqueous/acid conditions Where Y=H, the ring closure takes place after N-tosylation by palladium catalysis. The indole 3 is obtained by basic elimination of the N-tosyl group. The ester is reacted, at elevated temperatures, preferably from 80 to 130° C., with hydrazine in polar solvents such as the alcohols butanol and ethanol or else dimethylformamide. The hydrazide which accumulates in this connection is then reduced to the amide 4 under reductive conditions, such as using Raney nickel in alcohols under reflux.

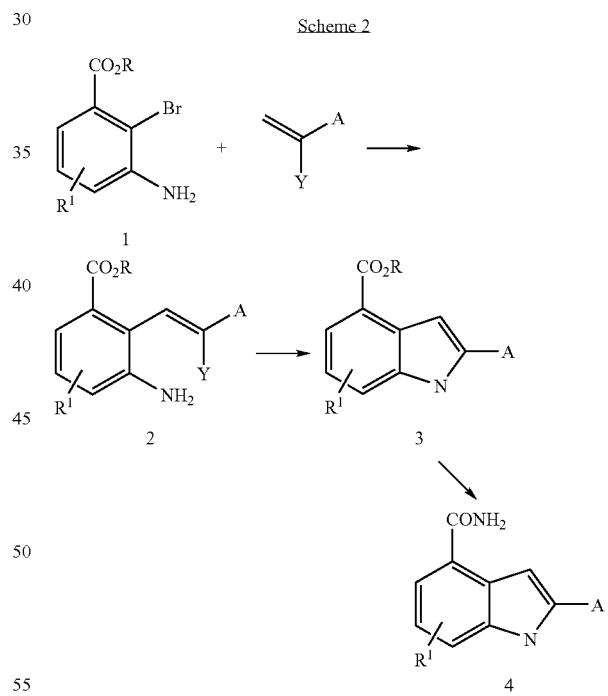

Scheme 2

The substituted indole derivatives which are contained in the present invention are inhibitors of the enzyme poly (ADP-ribose)polymerase or PARP (EC 2.4.2.30).

The inhibitory effect of the substituted indole derivatives Ia, IIa was ascertained using an enzyme test which was already known in the literature, with a $K_i$ value being determined as the measure of activity. In this way, the indole derivatives I–IV were quantitatively tested for their inhibitory effect on the enzyme poly(ADP-ribose)polymerase or PARP (EC 2.4.2.30).

The substituted indole derivatives of the general formulae I–IV are inhibitors of poly(ADP-ribose)polymerase (PARP) or, as it is also termed, poly(ADP-ribose)synthase (PARS) and can consequently be used for the treatment and prophylaxis of diseases which are linked to an increased activity of these enzymes.

The compounds of the formulae Ia, IIa can be employed for producing drugs for treating damage which occurs following ischemias and for prophylaxis where ischemias of various organs are expected.

Accordingly, the present indole derivatives of the general formulae Ia, IIa can be used for the treatment and prophylaxis of neurodegenerative diseases which occur following ischemia, trauma (craniocerebral trauma), hemorrhages, subarachnoidal bleeding and stroke, and of neurodegenerative diseases such as multiple infarct dementia, Alzheimer's disease and Huntington's disease, and of epilepsies, in particular of generalized epileptic attacks such as petit mal and tonic/clonic attacks and partial epileptic attacks, such as temporal lobe, and complex partial attacks, and, furthermore, for the treatment and prophylaxis of damage to the heart following cardiac ischemias and damage to the kidneys following renal ischemias, for example of acute kidney insufficiency, of acute kidney failure and of damage which occurs during and after a kidney transplant. Furthermore, the compounds of the general formulae Ia, IIa can be used for treating acute myocardial infarction and damage which occurs during and after its lysis by medical treatment (for example using TPA, Reteplase or Streptokinase or mechanically using a laser or rotablator), and of microinfarctions during and after heart valve replacement, aneurysm resections and heart transplants. The present indole derivatives Ia, IIa can likewise be used for treating revascularization of critically stenosed coronary arteries, for example in PCTA and bypass operations, and critically stenosed peripheral arteries, for example arteries of the leg. Furthermore, the indole derivatives Ia, IIa can be of use in the chemotherapy of tumors and their metastasization and be used for treating inflammations and rheumatic diseases, for example rheumatoid arthritis, and also for treating diabetes mellitus.

The drug preparations according to the invention contain a therapeutically effective quantity of the compounds Ia, IIa in addition to the customary pharmaceutical adjuvants.

For local external use, for example in powders, ointments or sprays, the active compounds can be present at the customary concentrations. As a rule, the active compounds are present in a quantity of from 0.001 to 1% by weight, preferably of from 0.001 to 0.1% by weight.

For internal use, the preparations are administered in individual doses. In an individual dose, from 0.1 to 100 mg is/are administered per kg of body weight. The preparations may be administered daily in one or more doses, depending on the nature and severity of the diseases.

In addition to the active compound, the drug preparations according to the invention comprise the customary excipients and diluents which correspond to the desired mode of administration. For local external use, it is possible to employ adjuvants which are customary in pharmaceutical technology, such as ethanol, isopropanol, ethoxylated castor oil, ethoxylated hydrated castor oil, polyacrylic acid, polyethylene glycol, polyethylene glycostearate, ethoxylated fatty alcohols, paraffin oil, vaseline and lanolin. Lactose, propylene glycol, ethanol, starch, talc and polyvinylpyrrolidone are, for example, suitable for internal use.

Furthermore the preparations can comprise antioxidants such as tocopherol and butylated hydroxyanisole and also butylated hydroxytoluene, taste-improving additives, stabilizers, emulsifiers and glidants.

The substances which the preparation contains in addition to the active compound, and also the substances employed in producing the pharmaceutical preparations, are toxicologically harmless and compatible with the relevant active compound. The drug preparations are produced in a customary manner, for example by mixing the active compound with other customary excipients and diluents.

The drug preparations may be administered in a variety of modes of administration, for example perorally, parenterally, such as intravenously by infusion, subcutaneously, intraperitoneally and topically. Thus, possible preparation forms are tablets, emulsions, infusion solutions, injection solutions, pastes, ointments, gels, creams, lotions, powders and sprays.

EXAMPLE A

Inhibition of the Enzyme Poly(ADP-ribose)polymerase or PARP (EC 2.4.2.30)

A 96-well microtiter plate (Falcon) is coated with histones (type II-AS; SIGMA H7755). For this, histones are dissolved up to a concentration of 50 µg/ml in carbonate buffer (0.05 M NaHCO$_3$; pH 9.4). The individual wells of the microtiter plate are incubated overnight with in each case 100 µl of this histone solution. The histone solution is then removed and the individual wells are incubated, at room temperature, with 200 µl of a 1% BSA (bovine serum albumin) solution in carbonate buffer for 2 hours. The plate is then washed three times with washing buffer (0.05% Tween10 in PBS). For the enzyme reaction, 50 µl of the enzyme reaction solution (5 µl of reaction buffer (1M Tris-HCl, pH 8.0, 100 mM MgCl$_2$, 10 mM DTT), 0.5 µl of PARP (c=0.22 µg/µl), 4 µl of activated DNA (SIGMA D-4522, 1 mg/ml in water), 40.5 µl of H$_2$O) are preincubated, in each well, for 10 minutes with 10 µl of an inhibitor solution. The enzyme reaction is started by adding 40 µl of a substrate solution (4 µl of reaction buffer (see above), 8 µl of NAD solution (100 µM in H$_2$O), 28 µl of H$_2$O). The reaction time is 20 minutes at room temperature The reaction is stopped by washing three times with washing buffer (see above). There then follows a one-hour incubation at room temperature, during which time the plate is incubated with a specific anti-poly-ADP-ribose antibody. The antibody employed was a monoclonal "10H", anti-poly(ADP-ribose) antibody (Kawamaitsu H et al. (1984) Monoclonal antibodies to poly (adenosine diphosphate ribose) recognize different structures. Biochemistry 23, 3771–3777). Polyclonal antibodies can be used in exactly the same way.

The antibodies were used in a 1:5000 dilution in antibody buffer (1% BSA in PBS; 0.05% Tween20). After the plate has been washed three times with washing buffer, there then follows a one-hour incubation at room temperature with the secondary antibody. In this case, use was made, for the monoclonal antibody, of an anti-mouse IgG coupled to peroxidase (Boehringer Mannheim) and, for the rabbit antibody, of an anti-rabbit IgG coupled to peroxidase (SIGMA A-6154), with each of these secondary antibodies being used in a 1:10000 dilution in antibody buffer. After the plate has been washed three times with washing buffer, the color reaction is effected using 100 µl of color reagent (SIGMA, TMB Readymix, T8540)/well at room temperature for approx. 15 min. The color reaction is stopped by adding 100 µl of 2M H$_2$SO$_4$. A measurement is then taken immediately (450 nm against 620 nm; "Easy Reader" ELISA plate reading appliance EAR340AT, SLT Labinstruments, Austria). The $IC_{50}$ value of an inhibitor under measurement is the concentration of the inhibitor at which the change in color concentration is half the maximum.

The following compounds according to the invention can be prepared using the above-described methods:

2-(4(4-n-Propylpiperazin-1-yl)phenyl)-1H-indole-4-carboxamide
2-(4-Piperazin-1-ylphenyl)-1H-indole-4-carboxamide
2-(4(4-Isopropylpiperazin-1-yl)phenyl)-1H-indole-4-carboxamide
2-(4(4-Benzylpiperazin-1-yl)phenyl)-1H-indole-4-carboxamide
2-(4(4-n-Butylpiperazin-1-yl)phenyl)-1H-indole-4-carboxamide
2-(4(4-Ethylpiperazin-1-yl)phenyl)-1H-indole-4-carboxamide
2-(4-(2-N,N-Dimethylaminoeth-1-yloxy)phenyl)-1H-indole-4-carboxamide
2-(4-(2-Pyrrolidin-1-yleth-1-yloxy)phenyl)-1H-indole-4-carboxamide
2-(4-(2-Piperidin-1-yleth-1-yloxy)phenyl)-1H-indole-4-carboxamide
2-(4-(2-Piperazin-1-yleth-1-yloxy)phenyl)-1H-indole-4-carboxamide
2-(4-(2-(4-Methylpiperazin-1-yl)eth-1-yloxy)phenyl)-1H-indole-4-carboxamide
2-(4-(2-(4-Propylpiperazin-1-yl)eth-1-yloxy)phenyl)-1H-indole-4-carboxamide
2-(4-(2-(4-Ethylpiperazin-1-yl)eth-1-yloxy)phenyl)-1H-indole-4-carboxamide
2-(4-(2-(4-Benzylpiperazin-1-yl)eth-1-yloxy)phenyl)-1H-indole-4-carboxamide
2-(4-(2-(4-Acetamidopiperazin-1-yl)eth-1-yloxy)phenyl)-1H-indole-4-carboxamide
2-(4-(2-(4-Benzanidopiperazin-1-yl)eth-1-yloxy)phenyl)-1H-indole-4-carboxamide
2-(4-Homopiperazin-1-ylphenyl)-1H-indole-4-carboxamide
2-(4(4-Methylhomopiperazin-1-yl)phenyl)-1H-indole-4-carboxamide
2-(4(4-Benzylhomopiperazin-1-yl)phenyl)-1H-indole-4-carboxamide
2-(4-(4-n-Butylhomopiperazin-1-yl)phenyl)-1H-indole-4-carboxamide
2-(4(4-Ethylhomopiperazin-1-yl)phenyl)-1H-indole-4-carboxamide
2-(4-Methoxyphenyl)-1H-indole-4-carboxamide
2-(4-Chlorophenyl)-1H-indole-4-carboxamide
2-(4-Aminophenyl)-1H-indole-4-carboxamide
2-(4-Methylphenyl)-1H-indole-4-carboxamide
2-(4-Phenylphenyl)-1H-indole-4-carboxamide
2-(4-Isopropylphenyl)-1H-indole-4-carboxamide
2-(4-Fluorophenyl)-1H-indole-4-carboxamide
2-(4-Trifluoromethylphenyl)-1H-indole-4-carboxamide
2-(3-Methoxyphenyl)-1H-indole-4-carboxamide
2-(3-Chlorophenyl)-1H-indole-4-carboxamide
2-(3-Aminophenyl)-1H-indole-4-carboxamide
2-(3-Methylphenyl)-1H-indole-4-carboxamide
2-(3-Phenylphenyl)-1H-indole-4-carboxamide
2-(3-Isopropylphenyl)-1H-indole-4-carboxamide
2-(3-Fluorophenyl)-1H-indole-4-carboxamide
2-(3-Trifluoromethylphenyl)-1H-indole-4-carboxamide
2-Piperidin-4-yl-1H-indole-4-carboxamide
2-(1-Methylpiperidin-4-yl)-1H-indole-4-carboxamide
2-(1-n-Propylpiperidin-4-yl)-1H-indole-4-carboxamide
2-(1-Benzylpiperidin-4-yl)-1H-indole-4-carboxamide
2-(1-n-Butylpiperidin-4-yl)-1H-indole-4-carboxamide
2-(1-Isopropylpiperidin-4-yl)-1H-indole-4-carboxamide
2-Pyridin-4-yl-1H-indole-4-carboxamide
2-Pyridin-3-yl-1H-indole-4-carboxamide
2-Pyridin-2-yl-1H-indole-4-carboxamide
2-Thien-2-yl-1H-indole-4-carboxamide
2-Thien-3-yl-1H-indole-4-carboxamide
2-Indol-3-yl-1H-indole-4-carboxamide
2-Indol-5-yl-1H-indole-4-carboxamide
2-Indol-2-yl-1H-indole-4-carboxamide
2-Quinolin-3-yl-1H-indole-4-carboxamide
2-Quinolin-2-yl-1H-indole-4-carboxamide
2-Quinolin-4-yl-1H-indole-4-carboxamide
2-Isoquinolin-1-yl-1H-indole-4-carboxamide
2-Isoquinolin-3-yl-1H-indole-4-carboxamide
2-Quinoxalin-2-yl-1H-indole-4-carboxamide
2-Naphth-2-yl-1H-indole-4-carboxamide
2-Naphth-1-yl-1H-indole-4-carboxamide
2-(2(N,N-Dimethylamino)eth-1-ylamino)phenyl)-1H-indole-4-carboxamide
2-(2(N,N-Diethylamino)eth-1-ylamino)phenyl)-1H-indole-4-carboxamide
2-(2-Piperidin-1-yleth-1-ylamino)phenyl)-1H-indole-4-carboxamide
2-(2-Pyrrolidin-1-yleth-1-ylamino)phenyl)-1H-indole-4-carboxamide
2-(3(N,N-Dimethylamino)prop-1-ylamino)phenyl)-1H-indole-4-carboxamide
2-(3(N,N-Diethylamino)prop-1-ylamino)phenyl)-1H-indole-4-carboxamide
2-(3-Piperidin-1-ylprop-1-ylamino)phenyl)-1H-indole-4-carboxamide
2-(3-Pyrrolidin-1-ylprop-1-ylamino)phenyl)-1H-indole-4-carboxamide
2-Cyclohexyl-1H-indole-4-carboxamide
2-(cis-4-Aminocyclohex-1-yl)-1H-indole-4-carboxamide
2-(4-Methoxycyclohex-1-yl)-1H-indole-4-carboxamide
2-(4(4-n-Propylpiperazin-1-yl)phenyl)-1,3,4,5-tetrahydro-6H-azepino[5,4,3-c,d]indol-6-one
2-(4-Piperazin-1-ylphenyl)-1,3,4,5-tetrahydro-6H-azepino[5,4,3-c,d]indol-6-one
2-(4(4-Isopropylpiperazin-1-yl)phenyl)-1,3,4,5-tetrahydro-6H-azepino[5,4,3-c,d]indol-6-one
2-(4(4-Benzylpiperazin-1-yl)phenyl)-1,3,4,5-tetrahydro-6H-azepino[5,4,3-c,d]indol-6-one
2-(4(4-n-Butylpiperazin-1-yl)phenyl)-1,3,4,5-tetrahydro-6H-azepino[5,4,3-c,d]indol-6-one
2-(4(4-Ethylpiperazin-1-yl)phenyl)-1,3,4,5-tetrahydro-6H-azepino[5,4,3-c,d]indol-6-one
2-(4-(2-N,N-Dimethylaminoeth-1-yloxy)phenyl)-1,3,4,5-tetrahydro-6H-azepino[5,4,3-c,d]indol-6-one
2-(4-(2-Pyrrolidin-1-yleth-1-yloxy)phenyl)-1,3,4,5-tetrahydro-6H-azepino[5,4,3-c,d]indol-6-one
2-(4-(2-Piperidin-1-yleth-1-yloxy)phenyl)-1,3,4,5-tetrahydro-6H-azepino[5,4,3-c,d]indol-6-one
2-(4-(2-Piperazin-1-yleth-1-yloxy)phenyl)-1,3,4,5-tetrahydro-6H-azepino[5,4,3-c,d]indol-6-one
2-(4-(2-(4-Methylpiperazin-1-yl)eth-1-yloxy)phenyl)-1,3,4,5-tetrahydro-6H-azepino[5,4,3-c,d]indol-6-one
2-(4-(2-(4-Propylpiperazin-1-yl)eth-1-yloxy)phenyl)-1,3,4,5-tetrahydro-6H-azepino[5,4,3-c,d]indol-6-one
2-(4-(2-(4-Ethylpiperazin-1-yl)eth-1-yloxy)phenyl)-1,3,4,5-tetrahydro-6H-azepino[5,4,3-c,d]indol-6-one
2-(4-(2-(4-Benzylpiperazin-1-yl)eth-1-yloxy)phenyl)-1,3,4,5-tetrahydro-6H-azepino[5,4,3-c,d]indol-6-one
2-(4-(2-(4-Acetamidopiperazin-1-yl)eth-1-yloxy)phenyl)-1,3,4,5-tetrahydro-6H-azepino[5,4,3-c,d]indol-6-one 2-(4-(2-(4-Benzamidopiperazin-2-yl)eth-1-yloxy)phenyl)-1,3,4,5-tetrahydro-6H-azepino[5,4,3-c,d]indol-6-one
2-(4-Homopiperazin-1-ylphenyl)-1,3,4,5-tetrahydro-6H-azepino[5,4,3-c,d]indol-6-one
2-(4(4-Methylhomopiperazin-1-yl)phenyl)-1,3,4,5-tetrahydro-6H-azepino[5,4,3-c,d]indol-6-one
2-(4(4-Benzylhomopiperazin-1-yl)phenyl)-1,3,4,5-tetrahydro-6H-azepino[5,4,3-c,d]indol-6-one
2-(4-(4-n-Butylhomopiperazin-1-yl)phenyl)-1,3,4,5-tetrahydro-6H-azepino[5,4,3-c,d]indol-6-one
2-(4(4-Ethylhomopiperazin-1-yl)phenyl)-1,3,4,5-tetrahydro-6H-azepino[5,4,3-c,d]indol-6-one
2-Piperidin-4-yl-1,3,4,5-tetrahydro-6H-azepino[5,4,3-c,d]indol-6-one
2-(1-Methylpiperidin-4-yl)-1,3,4,5-tetrahydro-6H-azepino[5,4,3-c,d]indol-6-one
2-(1-n-Propylpiperidin-4-yl)-1,3,4,5-tetrahydro-6H-azepino[5,4,3-c,d]indol-6-one
2-(1-Benzylpiperidin-4-yl)-1,3,4,5-tetrahydro-6H-azepino[5,4,3-c,d]indol-6-one
2-(1-n-Butylpiperidin-4-yl)-1,3,4,5-tetrahydro-6H-azepino[5,4,3-c,d]indol-6-one
2-(1-Isopropylpiperidin-4-yl)-1,3,4,5-tetrahydro-6H-azepino[5,4,3-c,d]indol-6-one
2-Pyridin-4-yl-1,3,4,5-tetrahydro-6H-azepino[5,4,3-c,d]indol-6-one
2-Pyridin-3-yl-1,3,4,5-tetrahydro-6H-azepino[5,4,3-c,d]indol-6-one
2-Pyridin-2-yl-1,3,4,5-tetrahydro-6H-azepino[5,4,3-c,d]indol-6-one
2-Thien-2-yl-1,3,4,5-tetrahydro-6H-azepino[5,4,3-c,d]indol-6-one
2-Thien-3-yl-1,3,4,5-tetrahydro-6H-azepino[5,4,3-c,d]indol-6-one
2-Indol-3-yl-1,3,4,5-tetrahydro-6H-azepino[5,4,3-c,d]indol-6-one
2-Indol-5-yl-1,3,4,5-tetrahydro-6H-azepino[5,4,3-c,d]indol-6-one
2-Indol-2-yl-1,3,4,5-tetrahydro-6H-azepino[5,4,3-c,d]indol-6-one
2-Quinolin-3-yl-1,3,4,5-tetrahydro-6H-azepino[5,4,3-c,d]indol-6-one
2-Quinolin-2-yl-1,3,4,5-tetrahydro-6H-azepino[5,4,3-c,d]indol-6-one
2-Quinolin-4-yl-1,3,4,5-tetrahydro-6H-azepino[5,4,3-c,d]indol-6-one
2-Isoquinolin-1-yl-1,3,4,5-tetrahydro-6H-azepino[5,4,3-c,d]indol-6-one
2-Isoquinolin-3-yl-1,3,4,5-tetrahydro-6H-azepino[5,4,3-c,d]indol-6-one
2-Quinoxalin-2-yl-1,3,4,5-tetrahydro-6H-azepino[5,4,3-c,d]indol-6-one
2-Naphth-2-yl-1,3,4,5-tetrahydro-6H-azepino[5,4,3-c,d]indol-6-one
2-Naphth-1-yl-1,3,4,5-tetrahydro-6H-azepino[5,4,3-c,d]indol-6-one
2-(2(N,N-Dimethylamino)eth-1-ylamino)phenyl)-1,3,4,5-tetrahydro-6H-azepino[5,4,3-c,d]indol-6-one
2-(2(N,N-Diethylamino)eth-1-ylamino)phenyl)-1,3,4,5-tetrahydro-6H-azepino[5,4,3-c,d]indol-6-one
2-(2-Piperidin-1-yleth-1-ylamino)phenyl)-1,3,4,5-tetrahydro-6H-azepino[5,4,3-c,d]indol-6-one
2-(2-Pyrrolidin-1-yleth-1-ylamino)phenyl)-1,3,4,5-tetrahydro-6H-azepino[5,4,3-c,d]indol-6-one
2-(3(N,N-Dimethylamino)prop-1-ylamino)phenyl)-1,3,4,5-tetrahydro-6H-azepino[5,4,3-c,d]indol-6-one
2-(3(N,N-Diethylamino)prop-1-ylamino)phenyl)-1,3,4,5-tetrahydro-6H-azepino[5,4,3-c,d]indol-6-one
2-(3-Piperidin-1-ylprop-1-ylamino)phenyl)-1,3,4,5-tetrahydro-6H-azepino[5,4,3-c,d]indol-6-one
2-(3-Pyrrolidin-1-ylprop-1-ylamino)phenyl)-1,3,4,5-tetrahydro-6H-azepino[5,4,3-c,d]indol-6-one
2-Cyclohexyl-1,3,4,5-tetrahydro-6H-azepino[5,4,3-c,d]indol-6-one
2-(cis-4-Aminocyclohex-1-yl)-1,3,4,5-tetrahydro-6H-azepino[5,4,3-c,d]indol-6-one
2-(4-Methoxycyclohex-1-yl)-1,3,4,5-tetrahydro-6H-azepino[5,4,3-c,d]indol-6-one

We claim:

1. A compound of the formula I or II

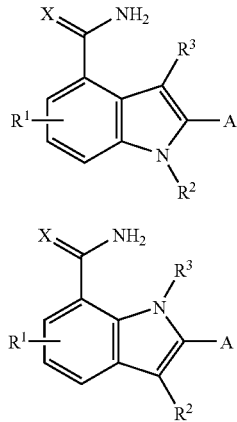

Where
X is S, O or NH, and
R¹ is hydrogen, chlorine, fluorine, bromine, iodine, branched or unbranched $C_1$–$C_6$-alkyl,
OH, $CF_3$, CN, $NR^{11}R^{12}$ or NH—CO—$R^{13}$, with $R^{11}$ and $R^{12}$, independently of each other, being hydrogen or $C_1$–$C_4$-alkyl, and $R^{13}$ being hydrogen, $C_1$–$C_4$-alkyl, $C_1$–$C_4$-alkylphenyl or phenyl and
$R^2$ is hydrogen, branched or unbranched $C_1$–$C_6$-alkyl, $C_1$–$C_4$-alkylphenyl or phenyl, and
$R^3$ is hydrogen, branched or unbranched $C_1$–$C_6$-alkyl, $C_1$–$C_4$-alkylphenyl, phenyl, COOH, COO—$C_1$–$C_4$-alkyl or $CONH_2$, with it being possible for each carbon atom in the alkyl chains to additionally carry one or two of the following substituents: OH, O—$C_1$–$C_4$-alkyl, $NR^{11}R^{12}$, COOH or COO—$C_1$–$C_4$-alkyl, and
A is an unsaturated, saturated or partially unsaturated monocyclic, bicyclic or tricyclic ring having at most 15 carbon atoms, such as phenyl, naphthalene, tetrahydronaphthalene, indan, fluorene, carbazole, cyclohexane, or an unsaturated, saturated or partially unsaturated monocyclic, bicyclic or tricyclic ring having at most 14 carbon atoms and from 0 to 5 nitrogen atoms, from 0 to 2 oxygen atoms and/or from 0 to 2 sulfur atoms, such as pyridine, thiophene, quinoline, quinoxaline, furan, imidazole, pyrrole, indole, benzimidazole, pyrimidine, pyrazine, benzofuran, benzothiophene, thiophene, quinazoline or isoxazole, which can in each case be additionally substituted by a $R^4$ radical and at most 3 $R^5$ radicals, and one or two carbon atoms and/or sulfur atoms may furthermore carry one or two =O groups, and $R^4$ is hydrogen or -(D)p-(E)s-$(F^1)$q-$G^1$-$(F^2)$r-$G^2G^3$, wherein when A is phenyl and p and s is O, $G^2$ is a bond and $R^5$ is not $NR^{11}R^{12}$, and D is S, $NR^{43}$ or O, E is phenyl,

—SO$_2$—, SO$_2$NH—, —NHCO—, CONH, —NHSO$_2$—, —NHCOCH$_2$X$_4$, and $X^4$ is S, O or NH, and $F^1$ is a straight-chain or branched, saturated or unsaturated $C_1$–$C_8$-group and $F^2$ independent of $F^1$ may have the same meaning as $F^1$, and $G^1$ is a bond or a saturated, partially unsaturated or unsaturated monocyclic, bicyclic or tricyclic ring with at most 15 carbon atoms, a saturated, partially unsaturated or unsaturated monocyclic, bicyclic or tricyclic ring with at most 14 carbon atoms and 0 to 5 nitrogen atoms, 0 to 2 oxygen atoms and/or 0 to 2 sulfur atoms, which each may be substituted with at most three different or equal $R^5$ radicals and wherein one or two carbon and/or sulfur atoms may furthermore carry one or two =O groups, and $G^2$ is $NR^{41}R^{42}$ and

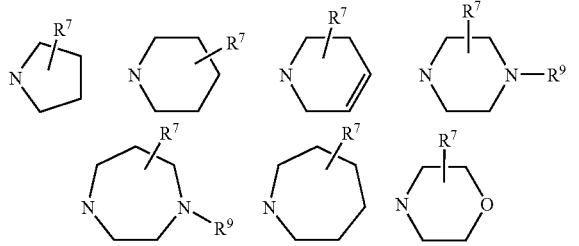

or a bond, and $G^3$ is hydrogen, a saturated, partially unsaturated or unsaturated monocyclic, bicyclic or tricyclic ring with at most 15 carbon atoms, a saturated, partially unsaturated or unsaturated monocyclic, bicyclic or tricyclic ring with at most 14 carbon atoms and 0 to 5 nitrogen atoms, 0 to 2 oxygen atoms and/or 0 to 2 sulfur atoms, which each may be substituted with at most three different or equal $R^5$ radicals and wherein one or two carbon and/or sulfur atoms may furthermore carry one or two =O groups, and p is 0 or 1, and s is 0 or 1, and q is 0 or 1, and r is 0 or 1, and $R^{41}$ is hydrogen, $C_{1-6}$-alkyl, wherein every carbon atoms may carry up to two $R^6$ radicals, phenyl, which may additionally carry at most two $R^6$ radicals, or (CH$_2$)$_t$-k, and $R^{42}$ is hydrogen, $C_1$–$C_6$-alkyl, —CO—$R^8$, SO$_2$—$R^8$, SO$_2$NH$_2$, —(C=N)—$R^8$ or —(C=N)—NHR$^8$, —=CO$_2$—$R^8$, and $R^{43}$ is hydrogen or $C_1$–$C_4$-alkyl, and t is 1, 2, 3 or 4, and K is $NR^{11}R^{12}$, $NR^{11}$—$C_1$–$C_4$-alkyl-phenyl, pyrrolidine, piperidine, 1,2,5,6-tetrahydropyridine, morpholine, homopiperidine, piperazine, which may be substituted with one $C_1$–$C_6$-alkyl group, or homopiperazine, which may be substituted with one $C_1$–$C_6$-alkyl group, and $R^5$ is hydrogen, chlorine, fluorine, bromine, iodine, branched or unbranched $C_1$–$C_6$-alkyl, OH, nitro, CF$_3$, CN, $NR^{11}R^{12}$, NH—CO—$R^{13}$ or O—$C_1$–$C_4$-alkyl, COR$^8$, $C_1$–$C_4$-alkyl-phenyl, phenyl, CO$_2$—$C_1$–$C_4$-alkyl, S—$C_1$–$C_4$-alkyl, wherein every carbon atom of the alkyl chains may additionally carry up to two $R^6$ radicals and wherein the alkyl chains may furthermore be unsaturated, and $R^6$ is hydrogen, chlorine, fluorine, bromine, iodine, branched or unbranched $C_1$–$C_6$-alkyl, OH, nitro CF$_3$, CN, $NR^{11}R^{12}$, NH—CO—$R^{13}$ or O—$C_1$–$C_4$-alkyl, and $R^7$ is hydrogen, $C_1$–$C_6$-alkyl, phenyl, where the ring can be additionally substituted by up to two $R^{71}$ radicals, or an amine $NR^{11}R^{12}$ or cyclic, saturated amine having 3 to 7 members, such as pyrrolidine, piperidine, etc., which may be substituted with one $C_1$–$C_6$ alkyl group, and homopiperazine, which may be substituted with one $C_1$–$C_6$-alkyl group, wherein groups $R^{11}$, $R^{12}$ and $R^{13}$ in K, $R^5$, $R^6$ and $R^7$ may have independently the same meaning as $R^1$ $R^{71}$ is OH, $C_1$–$C_6$-alkyl, O—$C_1$–$C_4$-alkyl, chlorine, bromine, iodine, fluorine, CF$_3$, nitro or NH$_2$, and $R^8$ is $C_1$–$C_6$-alkyl, CF$_3$, phenyl or $C_1$–$C_4$ alkylphenyl, where the ring can be additionally substituted by up to two $R^{81}$ radicals, and $R^{81}$ is OH, $C_1$–$C_6$-alkyl, O—$C_1$–$C_4$-alkyl, chlorine, bromine, iodine, fluorine, CF$_3$, nitro or NH$_2$, and $R^9$ is hydrogen, $C_1$–$C_6$-alkyl, CO$_2$—$C_1$–$C_4$-alkyl, COR$^8$, CO$_2$ $C_1$–$C_4$alkyl-phenyl, SO$_2$-phenyl, $C_1$–$C_4$ alkylphenyl or phenyl, where the phenyl rings can be additionally substituted by up to two $R^{91}$ radicals, and $R^{91}$ is OH, $C_1$–$C_6$-alkyl, O—$C_1$–$C_4$-alkyl, chlorine, bromine, iodine, fluorine, CF$_3$, nitro or NH$_2$, with the compounds 4-carboxamido-2-(1-ethylpiperidin-4-yl)-1H-indole and 4-carboxamido-2-(1-ethyl-1,2,3,6-tetrahydropyridine-4-yl)-1H-indole being excluded, and also their tautomeric forms, possible enantiomeric and diastereomeric forms, and their prodrugs.

2. A compound of the formula I or II as claimed in claim 1, wherein

X is O, and

R' is hydrogen, and all the other variables have the above-mentioned meanings.

3. A compound of the formula I or II as claimed in claim 1, wherein,

X is O, and $R^1$ is hydrogen, and

A is phenyl, cyclohexyl, piperidine, pyridine, pyrimidine or pyrazine, which compounds can be additionally substituted by one $R^4$ or at most 2 $R^5$, and all the other variables have the meanings as given in claim 1.

4. A compound of the formula I or II as claimed in claim 1, wherein

X is O, and

R' is hydrogen, and

A is phenyl, cyclohexyl, piperidine, pyridine, pyrimidine or pyrazine, which compounds can be additionally substituted by one $R^4$ or at most 2 $R^5$, and R[4] is -Dp-F$_{0.1}$-G[2]-G[3] with G[3] equal hydrogen, wherein, when A is phenyl and p is 1, D is not NR[43] and R[5] is not NR[11]R[12], and when A is phenyl and p is 0, G[2] is a bond
and R[5] is not NR[11]R[12],
D is O or NR[43], where R[43] is hydrogen or C$_1$–C$_3$-alkyl, and
F is C$_2$–C$_4$-alkyl, and
G[2] has the same meaning as given above, and
R[5] has the same meaning as given above.

5. The compounds of the general formulae I and II for producing drugs for treating neurodegenerative diseases and neuronal damage as in claim 1, with R[1], R[2], R[3] and X having the same meanings as given above and with it being possible for B to be hydrogen or a C$_1$–C$_6$ alkyl chain.

6. The compounds of the formulae I–II as claimed in claim 1 for producing drugs for treating neurodegenerative diseases and neuronal damage.

7. The compounds as claimed in claim 6 for treating such neurodegenerative diseases and neuronal damage which are induced by ischemia, trauma or hemorrhages.

8. The compounds as claimed in claim 6 for treating stroke and craniocerebral trauma.

9. The compounds as claimed in claim 6 for treating Alzheimer's disease, Parkinson's disease and Huntington's disease.

10. The compounds of the formulae I–II as claimed in claim 1 for producing drugs for the treatment or prophylaxis of damage due to ischemias.

11. The compounds of the formulae I–II as claimed in claim 1 for producing drugs for treating epilepsies, in particular generalized epileptic attacks, such as petit mal and tonic/clonic attacks and partial epileptic attacks, such as temporal lobe, and complex partial attacks.

12. The compounds of the formulae I–II as claimed in claim 1 for producing drugs for the treatment of damage to the kidneys following renal ischemias and for treatment during and after kidney transplants.

13. The compounds of the formulae I–II as claimed in claim 1 for producing drugs for treating damage to the heart following cardiac ischemias.

14. The compounds of the formulae I–II as claimed in claim 1 for producing drugs for treating microinfractions as, for example, during and after heart valve replacement, aneurysm resections and heart transplants.

15. The compounds of the formulae I–II as claimed in claim 1 for producing drugs for treating coronary arteries which are critically stenosed in association with a revascularization, as, for example, in association with PTCA and bypass operations, or critically stenosed peripheral arteries, in particular arteries of the leg.

16. The compounds of the formulae I–II as claimed in claim 1 for producing drugs for treating acute myocardial infraction and damage during and after its medicinal or mechanical lysis.

17. The compounds of the formulae I–II as claimed in claim 1 for producing drugs for treating tumors and their metastasization.

18. The compounds of the formulae I–II as claimed in claim 1 for producing drugs for treating sepsis and septic shock.

19. The compounds of the formulae I–II as claimed in claim 1 for producing drugs for treating immunological diseases such as inflammations and rheumatic disorders, for example rheumatoid arthritis.

20. The compounds of the formula I–II as claimed in claim 1 for producing drugs for treating diabetes mellitus.

21. A compound of the formula I or II

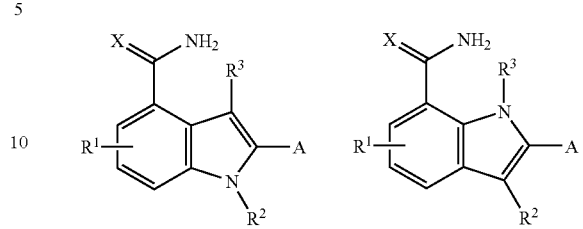

Where

X is S, O or NH, and

R' is hydrogen, chlorine, fluorine, bromine, iodine, branched or unbranched C$_1$–C$_6$-alkyl, OH, CF[3], CN, NR[11]R[12] or NH—CO—R[13], with R[11] and R[12], independently of each other, being hydrogen or C$_1$–C$_4$-alkyl, and R[13] being hydrogen, C$_1$–C$_4$-alkyl, C$_1$–C$_4$-alkylphenyl or phenyl and R[2] is hydrogen, branched or unbranched C$_1$–C$_6$-alkyl, C$_1$–C$_4$-alkylphenyl or phenyl, and R[3] is hydrogen, branched or unbranched C$_1$–C$_6$-alkyl, C$_1$–C$_4$-alkylphenyl, phenyl, COOH, COO—C$_1$–C$_4$-alkyl or CONH$_2$, with it being possible for each carbon atom in the alkyl chains to additionally carry one or two of the following substituents: OH, O—C$_1$–C$_4$-alkyl, NR[11]R[12], COOH or COO—C$_1$–C$_4$-alkyl, and A is an unsaturated, saturated or partially unsaturated monocyclic ring containing from 0 to 5 nitrogen atoms, from 0 to 2 oxygen atoms and/or from 0 to 2 sulfur atoms which can in each case be additionally substituted by an R[4] radical and at most three R[5] radicals and one or two carbon atoms and/or sulphur atoms may furthermore carry one or two =O groups.

R[4] is hydrogen or -(D)p-(E)s-(F[1])q-G[1]-(F[2])r-G[2]G[3], wherein when A is phenyl and p and s is 0, G[2] is a bond and R[5] is not NR[11]R[12], and D is S, NR[43] or O, E is phenyl,

—SO$_2$—, SO$_2$NH—, —NHCO—, CONH, —NHSO$_2$—, —NHCOCH$_2$X$_4$, and

X[4] is S, O or NH, and

F[1] is a straight-chain or branched, saturated or unsaturated C$_1$–C$_8$-group and F[2] independent of F[1] may have the same meaning as F[1], and G[1] is a bond or a saturated, partially unsaturated or unsaturated monocyclic, bicyclic or tricyclic ring with at most 15 carbon atoms, a saturated, partially unsaturated or unsaturated monocyclic, bicyclic or tricyclic ring with at most 14 carbon atoms and 0 to 5 nitrogen atoms, 0 to 2 oxygen atoms and/or 0 to 2 sulfur atoms, which each may be substituted with at most three different or equal R[5] radicals and wherein one or two carbon and/or sulfur atoms may furthermore carry one or two =O groups, and $G^2$ is $NR^{41}R^{42}$ and

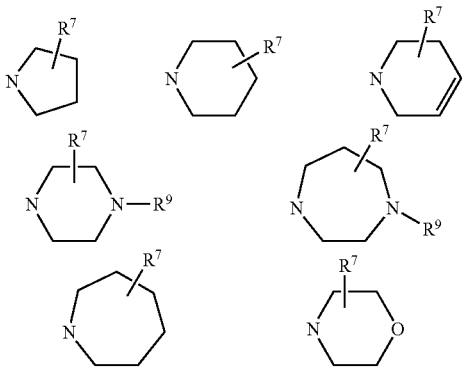

or a bond, and $G^3$ is hydrogen, a saturated, partially unsaturated or unsaturated monocyclic, bicyclic ortricyclic ring with at most 15 carbon atoms, a saturated, partially unsaturated or unsaturated monocyclic, bicyclic or tricyclic ring with at most 14 carbon atoms and 0 to 5 nitrogen atoms, 0 to 2 oxygen atoms and/or 0 to 2 sulfur atoms, which each may be substituted with at most three different or equal $R^5$ radicals and wherein one or two carbon and/or sulfur atoms may furthermore carry one or two =O groups, and p is 0 or 1, and s is 0 or 1, and q is 0 or 1, and r is 0 or 1, and $R^{41}$ is hydrogen, $C_{1-6}$-alkyl, wherein every carbon atoms may carry up to two $R^6$ radicals, phenyl, which may additionally carry at most two $R^6$ radicals, or $(CH_2)_t$-k, and $R^{42}$ is hydrogen, $C_1$–$C_6$-alkyl, —CO—$R^8$, $SO_2$—$R^8$, $SO_2NH_2$, —(C=N)—$R^8$ or —(C=N)—$NHR^8$, —=$CO_2$—$R^8$, and $R^{43}$ is hydrogen or $C_1$–$C_4$-alkyl, and t is 1, 2, 3 or 4, and K is $NR^{11}R^{12}$, $NR^{11}$—$C_1$–$C_4$-alkyl-phenyl, pyrrolidine, piperidine, 1,2,5,6-tetrahydropyridine, morpholine, homopiperidine, piperazine, which may be substituted with one $C_1$–$C_6$-alkyl group, or homopiperazine, which may be substituted with one $C_1$–$C_6$-alkyl group, and $R^5$ is hydrogen, chlorine, fluorine, bromine, iodine, branched or unbranched $C_1$–$C_6$-alkyl, OH, nitro, $CF_3$, ON, $NR^{11}R^{12}$, NH—CO—$R^{13}$ or O—$C_1$–$C_4$-alkyl, $COR^8$, $C_1$–$C_4$-alkyl-phenyl, phenyl, $CO_2$—$C_1$–$C_4$-alkyl, S—$C_1$–$C_4$-alkyl, wherein every carbon atom of the alkyl chains may additionally carry up to two $R^6$ radicals and wherein the alkyl chains may furthermore be unsaturated, and $R^6$ is hydrogen, chlorine, fluorine, bromine, iodine, branched or unbranched $C_1$–$C_6$-alkyl, OH, nitro $CF_3$, ON, $NR^{11}R^{12}$, NH—CO—$R^{13}$ or O—$C_1$–$C_4$-alkyl, and $R^7$ is hydrogen, $C_1C_6$-alkyl, phenyl, where the ring can be additionally substituted by up to two $R^{71}$ radicals, or an amine $NR^{11}R^{12}$ or cyclic, saturated amine having 3 to 7 members, such as pyrrolidine, piperidine, etc., which may be substituted with one $C_1$–$C_6$ alkyl group, and homopiperazine, which may be substituted with one $C_1$–$C_6$-alkyl group, wherein groups $R^{11}$, $R^{12}$ and $R^{13}$ in K, $R^5$, $R^6$ and $R^7$ may have independently the same meaning as $R^1$ $R^{71}$ is OH, $C_1$–$C_6$-alkyl, O—$C_1$–$C_4$-alkyl, chlorine, bromine, iodine, fluorine, $CF_3$, nitro or $NH_2$, and $R^8$ is $C_1$–$C_6$-alkyl, $CF_3$, phenyl or $C_1$–$C_4$ alkylphenyl, where the ring can be additionally substituted by up to two $R^{81}$ radicals, and $R^{81}$ is OH, $C_1$–$C_6$-alkyl, O—$C_1$–$C_4$-alkyl, chlorine, bromine, iodine, fluorine, $CF_3$, nitro or $NH_2$, and $R^9$ is hydrogen, $C_1$–$C_6$-alkyl, $CO_2$—$C_1$–$C_4$-alkyl, $COR^8$, $CO_2$ $C_1$–$C_4$alkyl-phenyl, $SO_2$-phenyl, $C_1$–$C_4$ alkylphenyl or phenyl, where the phenyl rings can be additionally substituted by up to two $R^{91}$ radicals, and $R^{91}$ is OH, $C_1$–$C_6$-alkyl, O—$C_1$–$C_4$-alkyl, chlorine, bromine, iodine, fluorine, $CF_3$, nitro or $NH_2$, with the compounds 4-carboxamido-2-(1-ethylpiperidin-4-yl)-1H-indole and 4-carboxamido-2-(1-ethyl-1,2,3,6-tetrahydropyridine-4-yl)-1H-indole being excluded, and also their tautomeric forms, possible enantiomeric and diastereomeric forms, and their prodrugs.

* * * * *

UNITED STATES PATENT AND TRADEMARK OFFICE
CERTIFICATE OF CORRECTION

PATENT NO. : 7,087,637 B2
APPLICATION NO. : 10/275574
DATED : August 8, 2006
INVENTOR(S) : Roland Grandel et al.

It is certified that error appears in the above-identified patent and that said Letters Patent is hereby corrected as shown below:

Claim 1, Col 20, line 38 should read as follows:

--$R^1$ is hydrogen, --.

Claim 1, Col 22, line 34 should read as follows:

--$CO_2$ $C_1$-$C_4$-alkyl-phenyl, $SO_2$-phenyl, --. .

Claim 2, Col 22, line 49 should read as follows:

--$R^1$ is hydrogen, --.

Claim 4, Col 22, line 64 should read as follows:

--$R^1$ is hydrogen, --.

Claim 21, Col 24, line 18 should read as follows:

--$R^1$ is hydrogen, --.

Claim 21, Col 25, line 3 should read as follows:

--bicyclic or tricyclic ring--.

Claim 21, Col 26, line 6 should read as follows:

--CN, $NR^{11}R^{12}$,--.

UNITED STATES PATENT AND TRADEMARK OFFICE
CERTIFICATE OF CORRECTION

PATENT NO. : 7,087,637 B2
APPLICATION NO. : 10/275574
DATED : August 8, 2006
INVENTOR(S) : Roland Grandel et al.

It is certified that error appears in the above-identified patent and that said Letters Patent is hereby corrected as shown below:

Claim 21, Col 26, line 14 should read as follows:

--CN, $NR^{11}R^{12}$,--.

Signed and Sealed this

Twenty-sixth Day of December, 2006

JON W. DUDAS
*Director of the United States Patent and Trademark Office*